US00PP07928P

United States Patent [19]

Winkel

[11] Patent Number: Plant 7,928

[45] Date of Patent: Aug. 4, 1992

[54] APPLE TREE AW-164

[75] Inventor: Arden C. Winkel, Hartford, Mich.

[73] Assignee: Inter-Plant Patent Marketing, Inc., Niagara-On-The-Lake, Canada

[21] Appl. No.: 444,453

[22] Filed: Dec. 1, 1989

[51] Int. Cl.[5] ..... A01H 5/00
[52] U.S. Cl. ..... Plt./35
[58] Field of Search ..... Plt. 35

[56] References Cited

U.S. PATENT DOCUMENTS

P.P. 3,578 6/1974 Campbell ..... Plt. 35
P.P. 6,190 5/1988 Sandidge ..... Plt. 35
P.P. 6,702 3/1989 Valle ..... Plt. 35

*Primary Examiner*—James R. Feyrer
*Attorney, Agent, or Firm*—Dykema Gossett

[57] ABSTRACT

A new variety of delicious apple tree discovered as a whole tree sport variety of "Redchief TM" and characterized by distinctive full blush coloring at maturity, inconspicuous lenticils, smooth and glassy finish, and early fruit color maturity.

7 Drawing Sheets

FIELD OF THE INVENTION

This invention relates generally to apple trees, and more specifically to a whole-tree mutation of the variety known as "Redchief TM".

BACKGROUND AND SUMMARY OF THE INVENTION

This distinct new apple cultivar was discovered in the orchard of Arden C. Winkel, 65444 66th Avenue, Hardford, Mich., 49057. It was found as a whole tree mutation in a planting of "Redchief TM" Red Delicious. With respect to those characteristics of AW-164 which have been systematically observed, it exhibits most of the usual characteristics of "Redchief TM" but develops a significantly brighter ruby red color over 95 to 100 percent of the surface with the color density developing 5 to 10 days earlier than "Redchief TM" as grown in the same geographical location and under the same conditions. Unlike the heavy stripe of "Redcielf TM", or the stripe of "Valley Spur", AW-164 is a blush. AS-164 shows some red color at the time the fruit is first formed and remains red throughout the growing season. Under the same conditions, "Redchief TM" is typically completely green at this time. Unlike "Redchief TM", the fruit is approximately 50% red 10 days after petal drop. The differences in color between AW-164 and "Redchief TM" and related sports is present at harvest and during post-harvest storage. During post-harvest storage, AW-164 holds brightness better than "Redchief TM". Unlike "Redchief TM", the fruit stem of AW-164 contains red pigmentation during the first 30 days of fruit growth. One factor which has been consistently observed between AW-164 and the parent and known related sports and which establishes that AW-164 is genotypically unique is the shape of AW-164 fruit. The fruit of AW-164 is markedly shorter than known related varieties, i.e. the bottom lobes of AW-164 are significantly less pronounced in length. Overall, AW-164 is more compact and, while somewhat vigorous, it is less so than the parent tree or those of known related sports. This new cultivar has been asexually propagated by budding and maintains the characteristics as described herein.

DETAILED DESCRIPTION OF THE INVENTION

Figure 1:
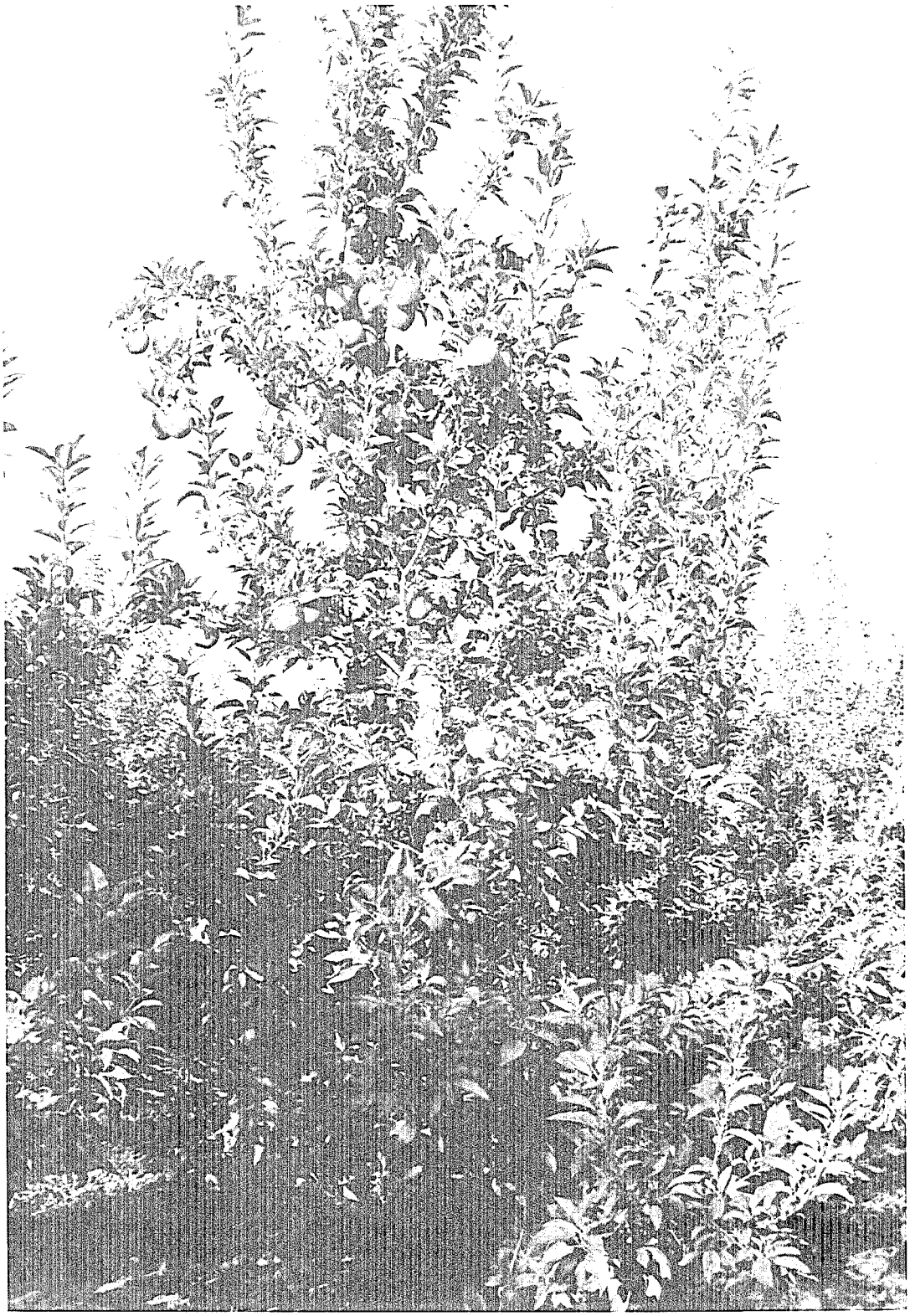
FIG. 1 depicts the AW-164 Apple Tree in elevational view; AW-164 is shown grafted onto a Malling 7 rootstock; the Malling 7 rootstock was planted in 1983, and bud grafted in 1985; the whole tree was transplanted in 1987.
Figure 2:
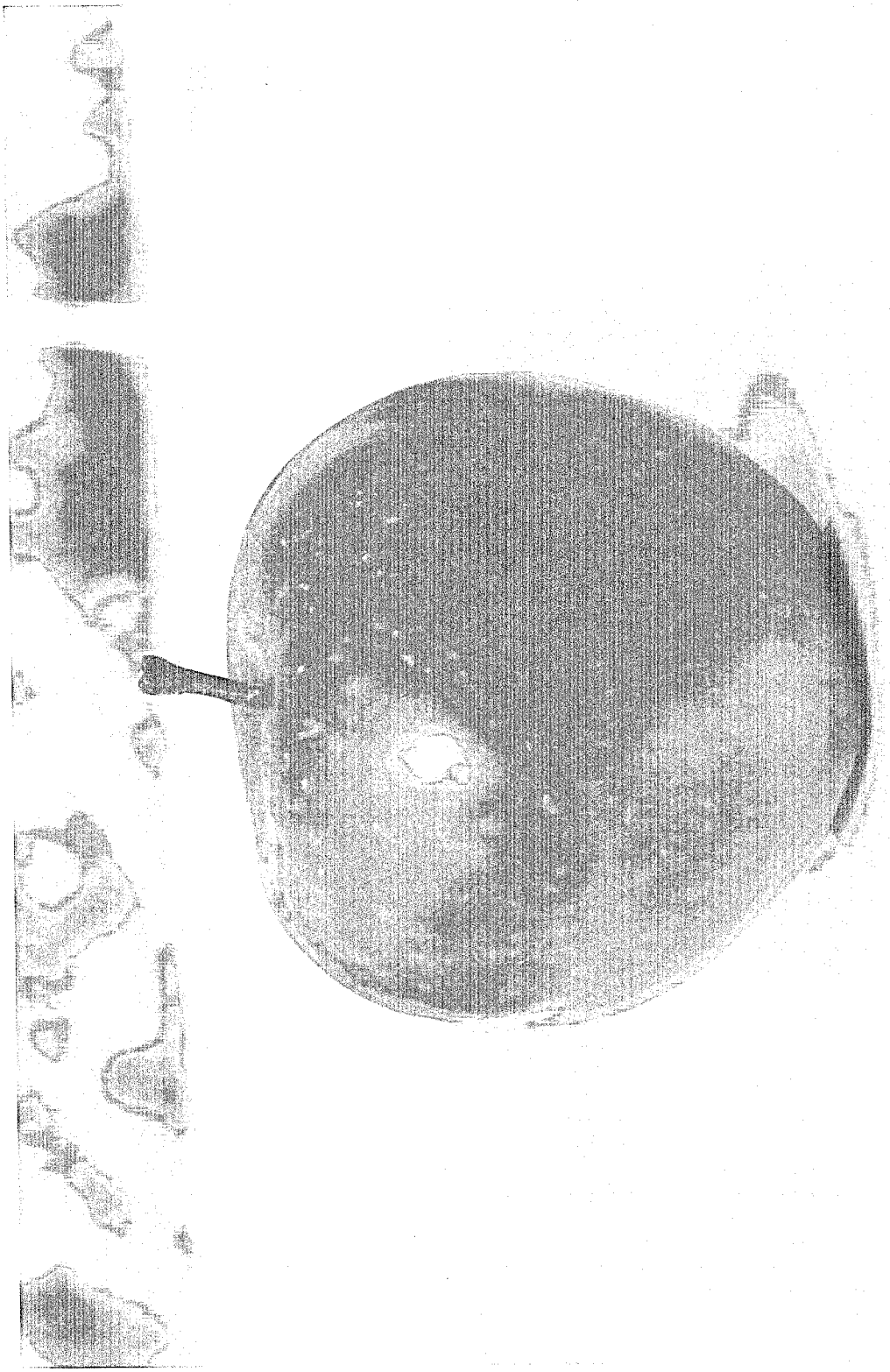
FIG. 2 is a front elevational view of one whole AW-164 fruit (polished).
Figure 3:
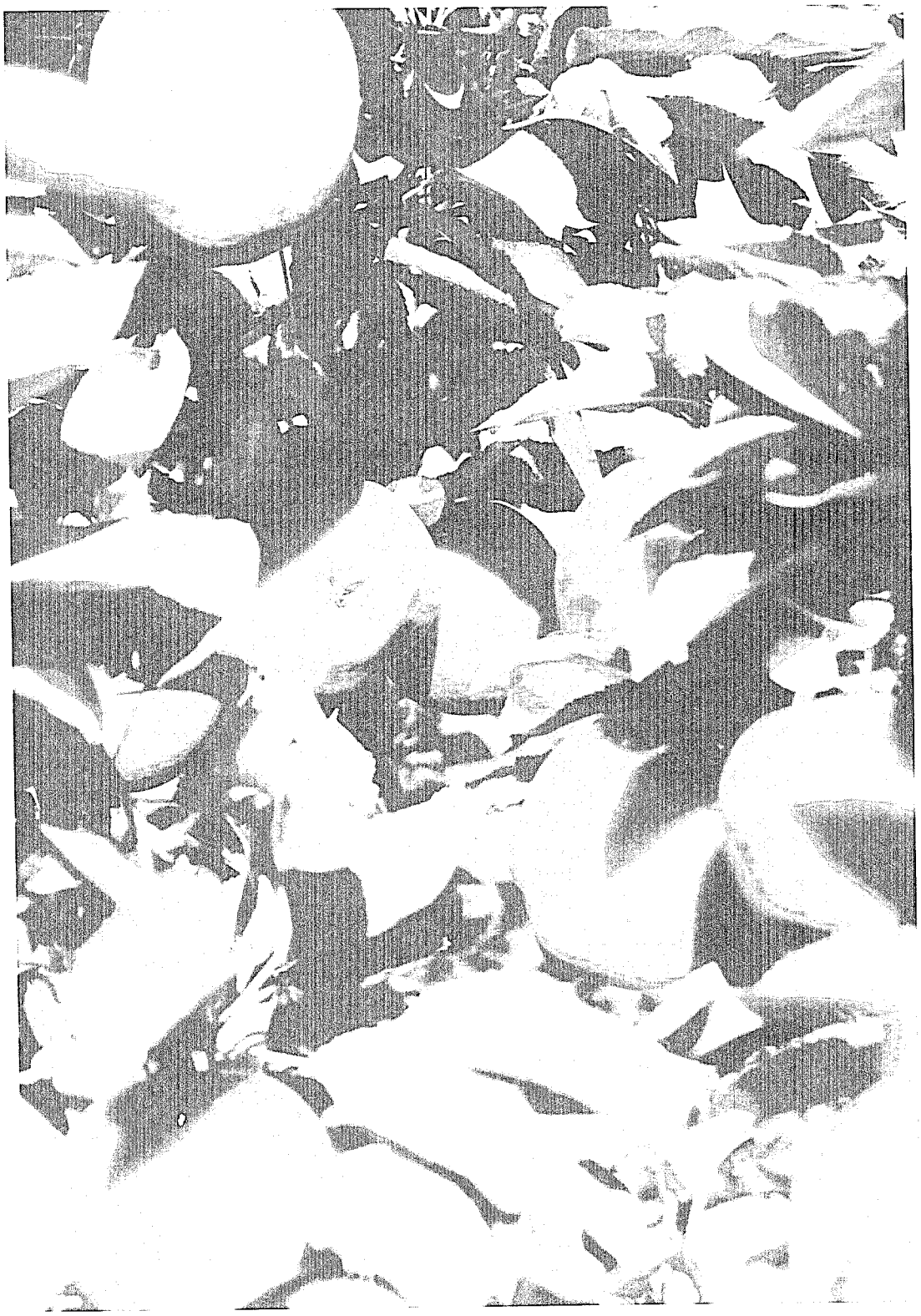
FIG. 3 illustrates a branch of AW-164 on the tree shown in FIG. 1 complete with fruit.
Figure 4:
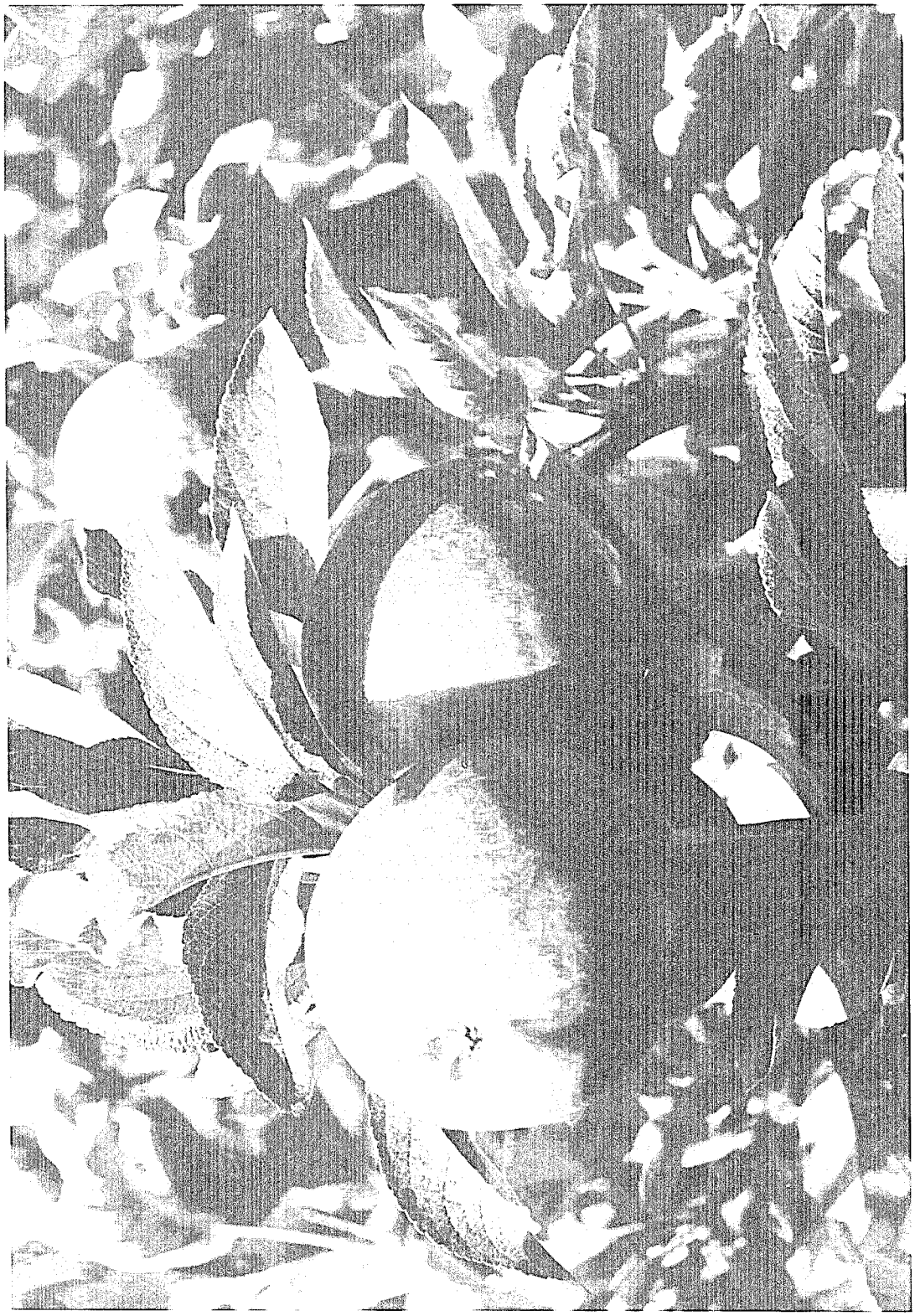
FIG. 4 depicts whole AW-164 fruit on a branch with leaf surfaces clearly shown.
Figure 5:
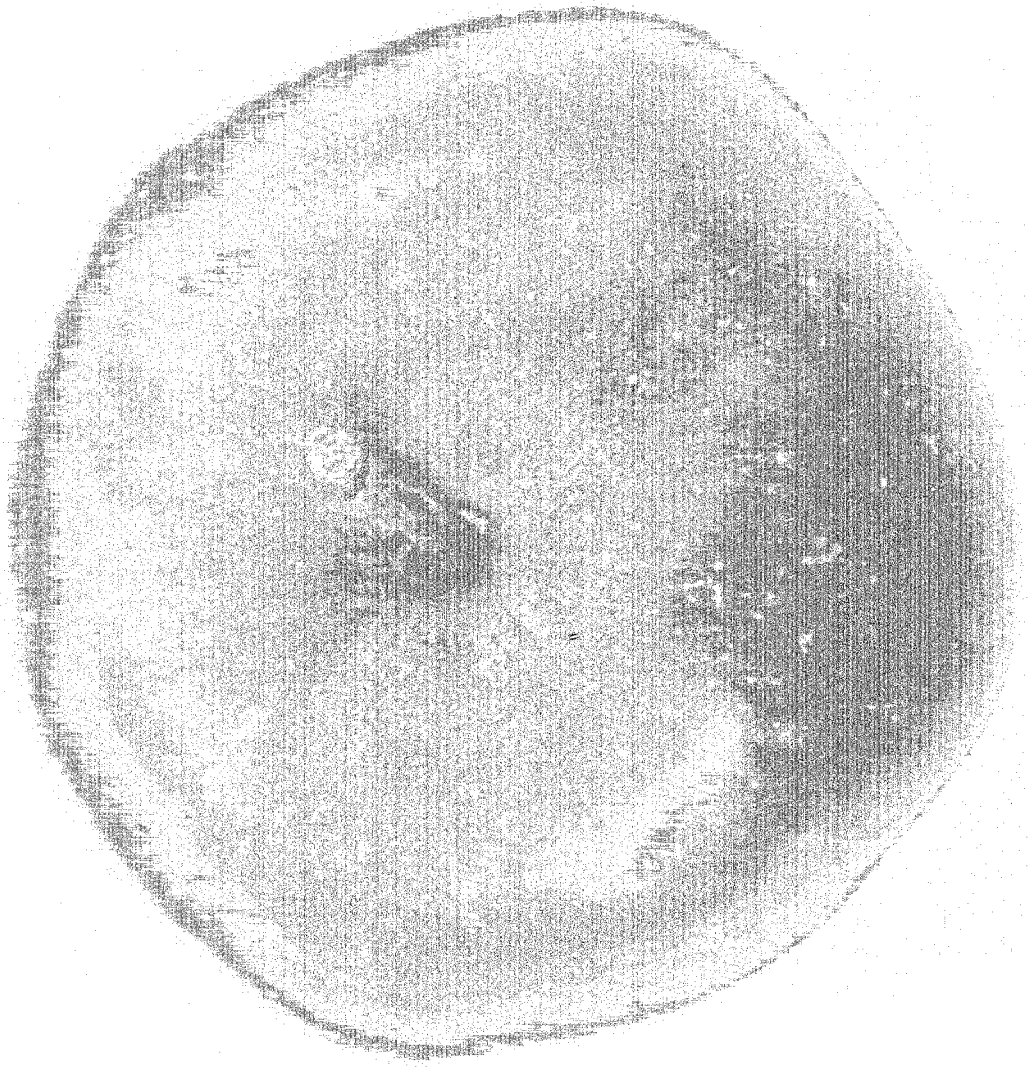
FIG. 5 is a top view of one AW-164 fruit (polished).
Figure 6:
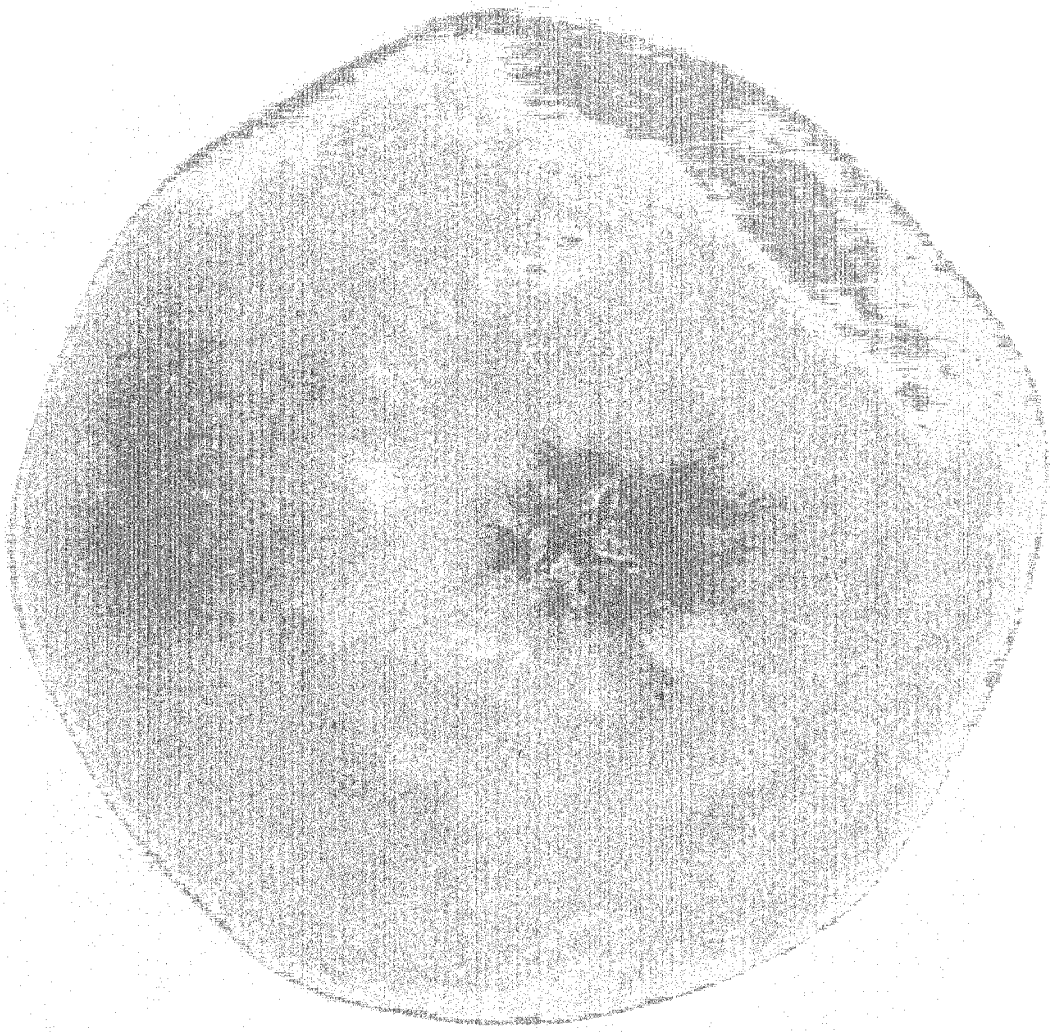
FIG. 6 is a bottom view of one AW-164 fruit (polished).
Figure 7:
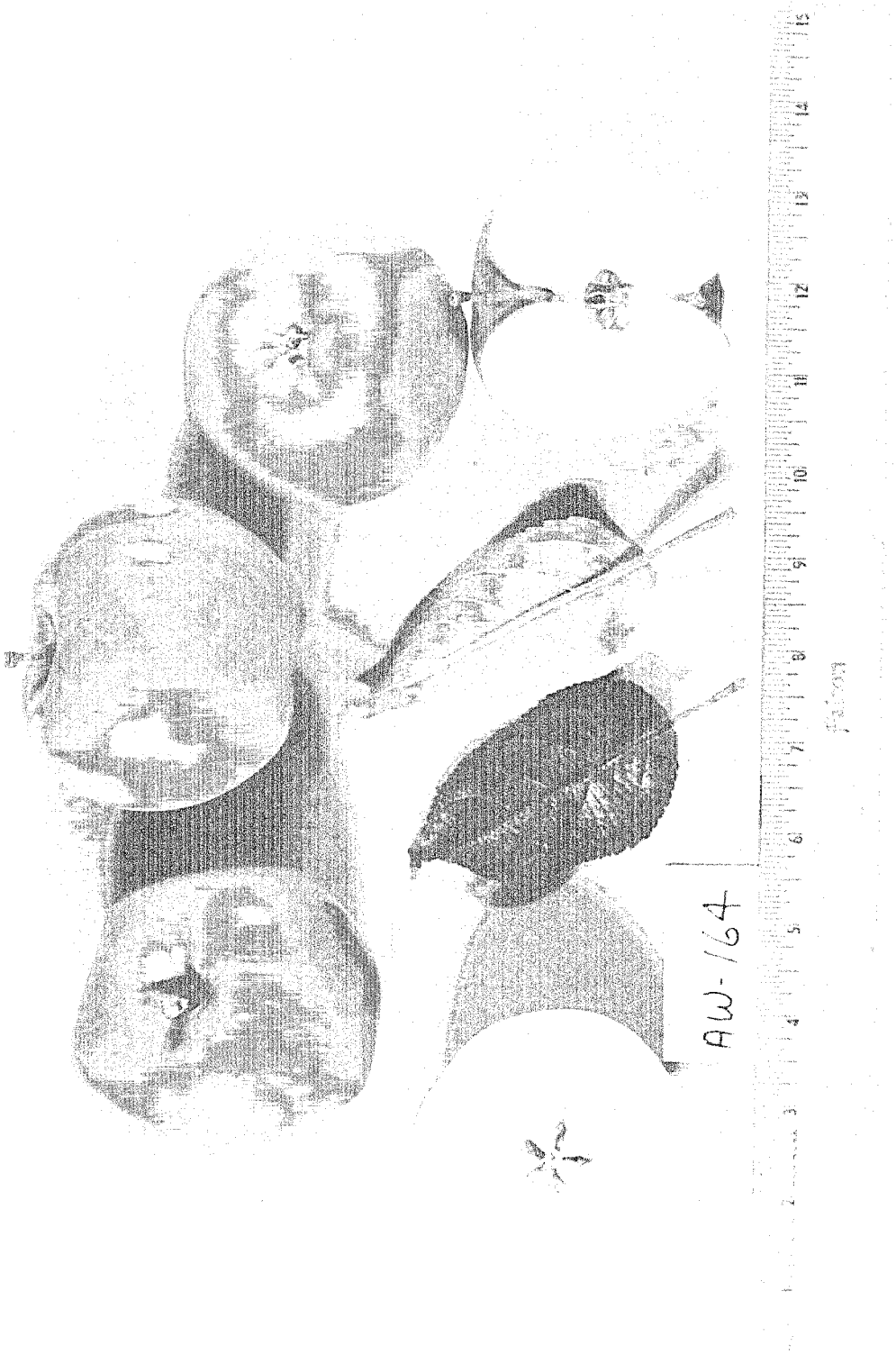
FIG. 7 depicts three whole AW-164 split fruits in different views along with top and bottom leaf surfaces; the slight difference in fruit color predominently reflects more extensive polishing and variation in lighting during photographing as well as variation in the photograph development process.

Color designations in the following descriptions are according to The Horticultural Colour Chart issued by the British Colour Council in collaboration with the British Horticultural Society.

Flower:

*Pedicel.*—1.4 to 2.2 cm in length.

*Corolla.*—2.3 to 3.0 cm in length.

*Color.*—While with pink at petal margins.

*Bloom date.*—In Southwestern Michigan, the bloom date for AW-164 is generally the same as that of "Redchief TM" in Southwestern Michigan under the same growing conditions. For the purposes of the following data, full bloom equal approximately 80 percent of blossoms on the adult tree. Bloom Dates of AW-164; 1987, May 5–6; 1988, May 12–14; 1989, May 19; 1990, May 3–5; 1991, May 4.

*Pollination requirement.*—AW-164 is cross-pollinated and is self-incompatible; the flower of AW-164 is diploid. Any viable pollen from apple trees which pollinate at the same time during which AW-164 is receptive is suitable. Appropriate pollinators are "Golden Delicious" and "Jonathen".

Fruit:

*Shape.*—Conic to regular, slightly ribbed.

*Size.*—Transverse diameter 7.0 to 7.5 cm. Axial diameter 6.5 to 7.0 cm. AW-164 fruit is estimated on limited data to be approximately 10%-20% (on average) shorter than the fruit of "Redchief TM".

*Color.*—Ruby Red (Plate 827) as a solid blush over 95 to 100 percent of the fruit surface.

*Skin.*—Smooth, waxy with medium, scattered, depressed, round dots.

*Stem.*—1.6 to 2.4 cm long, thick to slightly clubbed, extending to 0.6 to 1.0 cm above the shoulders of the cavity.

*Cavity.*—Obtuse, medium depth, smooth.

*Basin.*—Medium depth, broad, smooth, moderately lobed.

*Calyx.*—Persistent, partially open, separated at the base, slightly recurved.

*Stamens.*—Basal.

*Core lines.*—Meeting.

*Core.*—Distant, closed.

*Carpels.*—Emerginate, cordate, smooth.

*Seeds.*—0.6 to 0.8 cm in length, obtuse with some slightly tufted, dark brown.

*Flesh.*—Fine, white, crisp and juicy, sweet, aromatic, very good.

*Maturity season.*—Maturity by color development is slightly ahead to 10 days earlier than "Redchief TM". Maturity as analyzed by ethylene content of the fruit is the same as "Redchief TM" under the same growing conditions.

*Production regularity.*—AW-164 is more precocious than "Redchief TM". A greater number of less mature trees produce fruit than in the case of "Redchief TM". Alternating years of over-cropping and under-cropping have been noted.

*Ripening dates in* 1991.—in 1991 in Southwestern Michigan the ripened AW-164 fruit was first picked on Aug. 24th.

*Keeping Quality.*—Equal to "Redchief TM".

*Use.*—Desert quality for fresh eating.

*Sugar content.*—Sugar content as determined qualitatively varies somewhat from year to year (no quantitative data is available).

Tree:

*Growth habit.*—Somewhat less vigorous than "Redchief TM", upright, with spur-type fruiting habit. Annual terminal growth is 12 to 18 inches in juvenile trees and approximately 12 inches in mature trees, although terminal growth rate in Southwestern Michigan varies with the nature of the rootstock used.

*Leaves.*—Medium to large, dark green, simple, ovate to accuminate at the tips, simple serrations of the leaf margins. Upper surface smooth. Lower leaf surface moderately pubescent. Midrib raised with red color extending to the leaf base. Lateral veins white to light pink and slightly raised.

*Leaf size.*—Length 8.5 to 10.5 cm; Width 5.5 to 6.0 cm; Length/Width Ratio 1.7 to 1.8 cm.

*Disease susceptibility.*—From limited observations, AW-164 susceptibility to disease in Southerwestern Michigan is the same as "Redchief TM".

In particular, this new selection is believed to be a mutation of "Redchief TM" which it closely resembles but is distinguished most readily from the parent by the earlier and more intense development of red color. In addition, the lenticils on the fruit of AW-164 are less conspicuous in comparison with "Redchief TM" when comparable fruit of both varieties have been polished and otherwise prepared to the same manner. The fruit of AW-164 also has a smoother, glassier finish than that observed in "Redchief TM".

What is claimed:

1. The new and distinct apple tree AW-164, substantially as shown and described.

* * * * *